(12) United States Patent
Boocock

(10) Patent No.: US 6,642,399 B2
(45) Date of Patent: Nov. 4, 2003

(54) SINGLE-PHASE PROCESS FOR PRODUCTION OF FATTY ACID METHYL ESTERS FROM MIXTURES OF TRIGLYCERIDES AND FATTY ACIDS

(76) Inventor: David Gavin Brooke Boocock, 24 Bolland Crescent, Ajax, Ontario (CA), L1S 3G7

( * ) Notice: Subject to any disclaimer, the term of this patent is extended or adjusted under 35 U.S.C. 154(b) by 0 days.

(21) Appl. No.: 10/199,359

(22) Filed: Jul. 22, 2002

(65) Prior Publication Data

US 2003/0083514 A1 May 1, 2003

Related U.S. Application Data

(63) Continuation of application No. 09/639,717, filed on Aug. 16, 2000, now abandoned.
(60) Provisional application No. 60/149,810, filed on Aug. 19, 1999.

(30) Foreign Application Priority Data

Aug. 18, 1999 (CA) ............................................. 2280289

(51) Int. Cl.$^7$ ............................... C11C 1/00; C11C 3/00
(52) U.S. Cl. ........................... 554/167; 54/163; 54/169; 54/970
(58) Field of Search ................................. 554/167, 164, 554/163, 170

*Primary Examiner*—Deborah D. Carr
(74) *Attorney, Agent, or Firm*—Webb Ziesenheim Logsdon Orkin & Hanson P.C.

(57) ABSTRACT

A process for the esterification of a mixture of fatty acids and triglycerides. The process comprises forming a single phase solution of fatty acids and triglyceride in an alcohol selected from methanol and ethanol, the ratio of said alcohol to triglyceride being 15:1 to 35:1. The solution further comprises a co-solvent in an amount to form the single phase. In a first step, an acid catalyst for the esterification of the fatty acids is added. After a period of time, the acid catalyst is neutralized and a base catalyst for the transesterification of triglycerides is added. After a further period of time, esters are separated from the solution.

23 Claims, 2 Drawing Sheets

SINGLE-PHASE PROCESS FOR PRODUCTION OF FATTY ACID METHYL ESTERS FROM MIXTURES OF TRIGLYCERIDES AND FATTY ACIDS

This application is a continuation of U.S. application Ser. No. 09/639,717, filed Aug. 16, 2000, and now abandoned which claims the priority benefit of U.S. Application Serial No. 60/149,810, filed Aug. 19, 1999, and claims the priority benefit of Canadian Application 2,280,289, filed Aug. 18, 1999.

FIELD OF THE INVENTION

The present invention relates to the production of fatty acid methyl esters from mixtures of triglycerides and fatty acids. In particular, the invention relates to a single-phase process, which may be referred to as a two-step process, for production of fatty acid methyl esters from mixtures of triglycerides and fatty acids. The process does not require separation of any phases in intermediate steps in the process.

BACKGROUND OF THE INVENTION

The transesterification of vegetable oils to form esters, and in particular, methyl esters, has received considerable attention, primarily because the esters may be used as "biofuels" or "biodiesel". Biofuels are fuels derived from renewable resources such as naturally occurring fats and oils. Such fats and oils may be obtained from a variety of plant and animals. Biodiesel relates to the specific application to diesel fuel.

The major components of an oil or fat are fatty acid triglycerides, in which three long chain fatty acid moieties are joined to one glycerol moiety by ester linkages, particularly when the fats and oils are in the form of vegetable oils. Other sources of fats and oils contain a significant proportion of fatty acids. Such fatty acids may include lauric acid, palmitic acid, stearic acid, oleic acid and linoleic acid.

A number of manufacturing facilities have been built in Europe for the manufacture of biofuels, and similar facilities are planned for other countries.

The formation of vegetable oil methyl esters by the base-catalyzed reaction of triglycerides in the vegetable oil with methanol is a two-phase reaction, and is known to be slow. The problem of the slow reaction rate may be alleviated by the use of non-reactive co-solvents, which result in the conversion of the two-phase system into a single-phase system. Simple ethers, such as tetrahydrofuran (THF) and methyltertiarybutylether (MTBE), are particularly good co-solvents, as is described in Canadian Patent Application 2,131,654, published Mar. 9, 1996. Molar ratios of alcohol to triglyceride of at least 4.5:1 and more preferably at least about 6:1 are disclosed, with typical ratios being in the range of 6:1 to 8:1. The reaction is further discussed by D. G. B. Boocock et al in Biomass and Bioenergy Vol. 11, No. 1 pp 43–50 (1996).

Canadian Patent Application 2,131,654 states that free fatty acids are particularly troublesome components of fats and oils. In particular, when a transesterification of the oil (triglyceride) using a base catalyst is attempted in the presence of fatty acids, the free fatty acids form soaps on neutralization by the base catalyst.

U.S. Pat. No. 4,164,506 of Kawahara et al. discloses a process involving (a) esterification of free fatty acids in the presence of an acid catalyst, (b) allowing the product mixture to separate into a fat layer and an alcohol layer so as to obtain a refined fat layer, and (c) then subjecting the fat layer to transesterification with a base catalyst.

U.S. Pat. No. 4,695,411 of Stern et al. discloses a multi-step reaction involving acid transesterification with alcohol in the presence of 1–60% water and separating a glycerol phase that is obtained, reducing the free acidity of the remaining ester phase and then transesterification in the presence of a base catalyst.

U.S. Pat. No. 4,698,186 of Jeromin et al. discloses a process for reducing the free acid content of fats and oils by esterification with an alcohol in the presence of an acidic cation exchange resin.

U.S. Pat. No. 5,525,126 of Basu et al teaches esterification of mixtures of fats and oils by using a calcium acetate/barium acetate catalyst. However, the method requires elevated temperature (in excess of 200° C.) and pressure (approximately 500 psi). The reaction time (three hours) is long. These conditions render the process impractical and uneconomical.

U.S. Pat. No. 5,713,965 of Foglia et al. teaches use of lipases to transesterify mixtures of triglycerides and free fatty acids. The reactions require 4–16 hours to reach conversion rates of 95%, which is not practical for an industrial process.

Improvements in processes for the production of fatty acid methyl esters from mixtures of fatty acids and triglycerides are required. In particular, a process for the conversion of fatty acids and triglycerides to the corresponding ester in a manner that is fast, essentially complete and is cost effective for both capital and operating costs is required. Such a process would offer potential as an industrial process.

SUMMARY OF THE INVENTION

Processes for the production of fatty acid methyl esters from mixtures of triglycerides and fatty acids have now been found.

Accordingly, one aspect of the present invention provides a single phase process for the esterification of a mixture of fatty acids and triglycerides, comprising:
 (a) forming a solution of said fatty acid and triglycerides, an alcohol, an acid catalyst and a cosolvent at a temperature that is less than the boiling point of the solution, said alcohol being selected from the group consisting of methanol and ethanol, or mixtures thereof, and the ratio of said alcohol to said triglycerides and fatty acid being in the range of 15:1 to 35:1, the cosolvent being in an amount to effect formation of the single phase;
 (b) maintaining the solution for a period of time to effect acid-catalyzed esterification of the fatty acids;
 (c) neutralizing the acid catalyst and adding a base catalyst for the transesterification of said triglycerides; and
 (d) after a further period of time, separating esters from said solution.

In preferred embodiments of the invention, the triglyceride is selected from the group consisting of beef tallow, coconut oil, corn oil, cottonseed oil, lard, olive oil, palm oil, palm kernel oil, peanut oil, soybean oil, linseed oil, tung oil, sunflower oil, safflower oil, canola oil, rapeseed oil, sesame oil, babassu oil, perilla oil, oiticica oil, fish oils, menhaden oil, castor oil, Chinese tallow tree oil, Physic nut oil, Cuphea seed oil, microalgal oils, bacterial oils and fungal oils.

In a further embodiment of the invention, the cosolvent is selected from the group consisting of tetrahydrofuran, 1,4-dioxane, diethyl ether, methyltertiarybutylether and diisopropyl ether.

In another embodiment of the invention, the process is a continuous process.

BRIEF DESCRIPTION OF THE DRAWINGS

The present invention is illustrated by the embodiments shown in the drawing, in which.

DETAILED DESCRIPTION OF THE INVENTION

Figure 1:
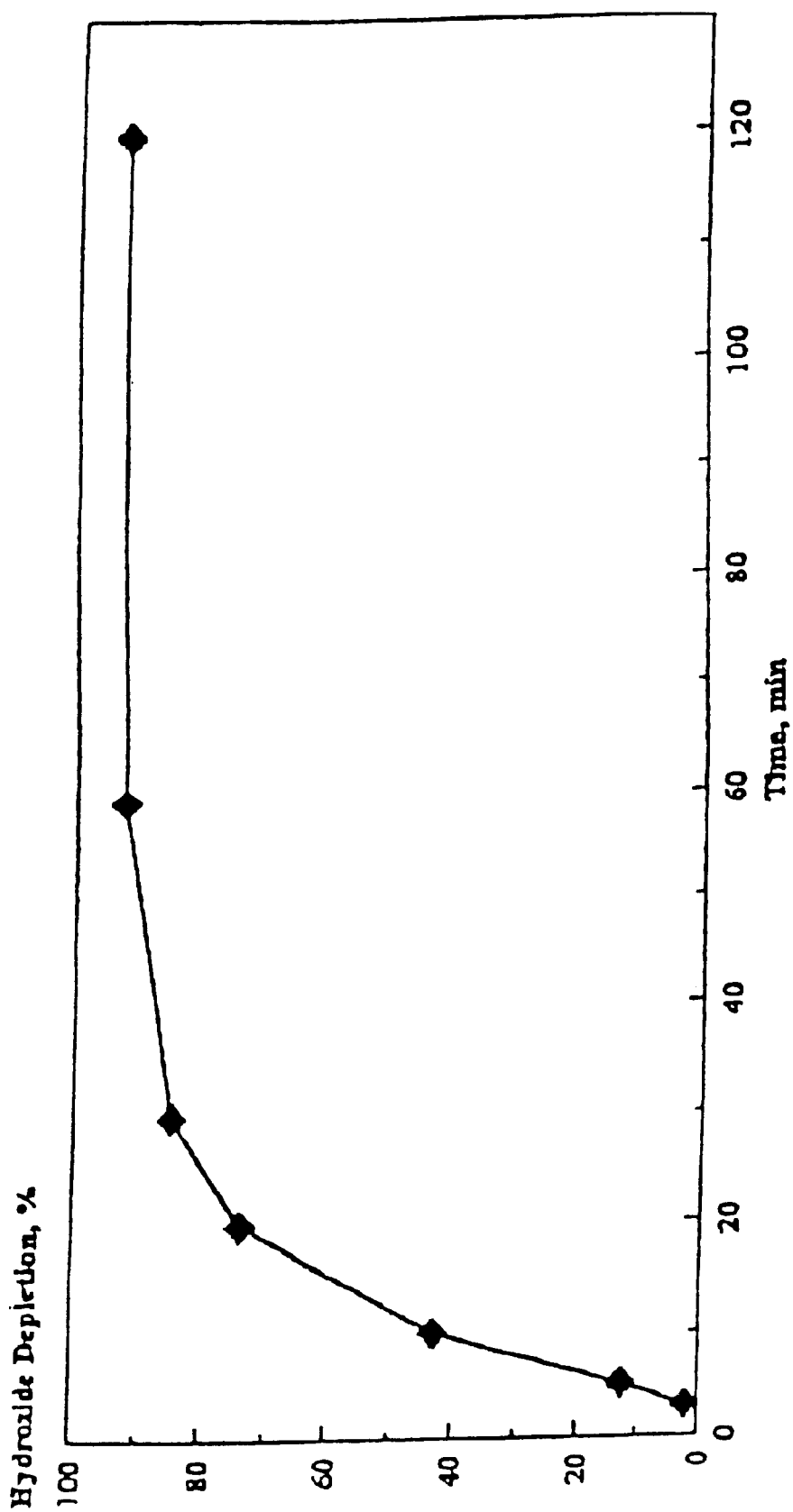
FIG. 1 is a graphical representation of depletion of hydroxide ion concentration with time during methanolysis, according to the prior art.

The present invention relates to the formation of esters from fats and oils in the presence of fatty acids. In particular, the present invention relates to the preparation of esters from mixtures of triglycerides and fatty acids. Although the formation of methyl esters is particularly discussed herein, which is the preferred embodiment, the esterification reaction may be carried out using either methanol or ethanol, or mixtures thereof. Methanol boils at 64.5° C. and ethanol boils at 78.3° C. The invention will be particularly described herein with reference to the use of methanol.

The invention provides a single-phase process for the conversion of a mixture of fatty acids and triglycerides. In the process, fatty acids are converted to methyl esters by an acid-catalyzed reaction with methanol. The solution is then neutralized and a base is added to catalyze the reaction of the triglycerides with methanol to form methyl esters. The entire reaction is carried out in the same phase, and steps to separate phases are not required.

A wide range of mixtures of fatty acids and triglycerides may be used, including the range from minor amounts of fatty acids in the mixture to minor amounts of triglycerides in the mixture.

In the process of the present invention, a single-phase solution of the mixture of fatty acid triglyceride and fatty acid is formed. The triglyceride and fatty acid are mixed with the alcohol viz. methanol or ethanol or mixtures thereof, in a ratio of alcohol: (triglyceride and fatty acid) that is in the range of 15:1 to 35:1. Cosolvent is added to effect formation of the single-phase solution. In the separate steps, an acid catalyst and then a base catalyst are added. The reaction solution should contain less than about 1% by weight of water, and preferably less than 0.5% by weight of water.

The mixture of fatty acids and triglycerides is preferably mixed with the alcohol, in the ratio required for the second stage of the reaction i.e. base-catalyzed conversion of the triglycerides to methyl esters. Cosolvents are preferably added at the same time for the same reason. The addition of methanol, with an appropriate amount of cosolvent, in molar ratios of methanol to fatty acid triglyceride of 15:1 to 35:1 results in substantial increases in both conversion and rate of conversion of triglyceride to methyl ester in the base-catalyzed step in the reaction. Preferred molar ratios are in the range of 20:1 to 30:1, and most preferably in the range of 25:1 to 30:1. The increased conversion and rate of conversion obtainable in the base-catalyzed step are illustrated in the Examples herein. It is believed that the use of such molar ratios and cosolvent also benefits the acid-catalyzed step of the reaction.

The composition subjected to formation of methyl esters is a mixture of triglycerides and fatty acids. Such mixtures may be obtained from a wide variety of sources, e.g. restaurants, meat processing operations and oils from distressed oil seeds. The present invention is particularly directed to use of sources of triglycerides that contain fatty acids, although the mixtures from such sources may be supplemented with other triglycerides and/or fatty acids.

Examples of supplemental sources of triglycerides include beef tallow, coconut oil, corn oil, cottonseed oil, lard, olive oil, palm oil, palm kernel oil, peanut oil, soybean oil, linseed oil, tung oil, sunflower oil, safflower oil, canola oil, rapeseed oil, sesame oil, babassu oil, perilla oil, oiticica oil, fish oils, menhaden oil, castor oil, Chinese tallow tree oil, Physic nut oil, Cuphea seed oil, microalgal oils, bacterial oils and fungal oils. While a range of vegetable oils may be used in the process of the present invention, it is particularly applicable to vegetable oils having at least 16 carbon atoms i.e. triglycerides having fatty acid moieties that are $C_{16}$ or higher.

An acid catalyst is required for the first stage of the reaction i.e. the formation of methyl esters from fatty acids. Preferred catalysts are soluble in the solution, with the most preferred catalyst being sulphuric acid. Other examples of acid catalysts include hydrochloric acid and trifluoroacetic acid.

The formation of methyl esters from the fatty acids is preferably carried out at atmospheric pressure and at a temperature at 60–65° C. i.e. close to the boiling point of methanol.

A cosolvent is added in at least an amount sufficient to form a single phase solution of the alcohol, fatty acid, fatty acid triglyceride and cosolvent. The cosolvent is preferably completely miscible with both the alcohol and the source of fatty acid triglyceride. The cosolvent preferably has a boiling point of less than about 120° C. to facilitate solvent removal after the reaction is complete. More preferably, the cosolvent has a boiling point similar to that of the alcohol. Preferred cosolvents are cyclic ethers, which have a hydrophilic oxygen atom capable of forming hydrogen bonds with water and alcohols, and a hydrophobic hydrocarbon portion capable of solubilizing many organic compounds. Examples of cosolvents are cyclic ethers such as tetrahydrofuran (THF) and 1,4-dioxane, diethyl ether, methyltertiarybutylether and diisopropyl ether.

The cosolvent is preferably anhydrous. Larger amounts of cosolvent can be added than are required to solubilize the oil or fat with satisfactory results.

The most preferred cosolvent is THF, especially for methanolysis, as un-reacted methanol and THF may be co-distilled and recycled at the end of the reaction. The amount of cosolvent needed depends on the particular source of fatty acid triglyceride, the alcohol being used and the cosolvent.

After a period of time e.g. about 30–60 minutes, the solution is neutralized by the addition of a base. In a preferred embodiment of the invention, the acid used in the conversion of the fatty acid to methyl esters is neutralized with anhydrous sodium carbonate, or a compound that results in the formation of sodium sulphate (if the acid is sulphuric acid). Water is formed as a by-product in the first stage of the reaction, and sodium sulphate forms a hydrate in the presence of water. Thus, water is removed from the reaction mixture. The amount of free water should be reduced to less than about 1% by weight, if necessary, and preferably to less than 0.5% by weight.

The base catalyst is typically sodium hydroxide or potassium hydroxide, although the corresponding methoxides may be used. The hydroxides are preferred because of safety considerations. Other soluble and insoluble base catalysts may be used.

The base catalyst should be substantially moisture free, and preferably stored under substantially anhydrous conditions. Prolonged contact of base catalysts with air should also be avoided, because water and carbon dioxide tend to diminish the effectiveness of the catalyst.

All steps of the reaction are carried out below the lower of the boiling points of the solvent and cosolvent. For methanolysis in the presence of THF (bp 67° C.), the temperature should be not more than about 65° C. viz. the boiling point of methanol. However, for ethanolysis using ethanol (b.p. 78° C.) in the presence of THF (b.p. 67° C.), the temperature should be not more than about 67° C. A range of temperature may be used. For instance, temperatures of less than 65° C. may be used, including temperatures at or below ambient temperature (15° C.). However, higher temperatures do increase the rate of reaction, and preferred temperatures are at least 50° C., especially at least 60° C., and preferably 60–65° C. It is preferred that the acid-catalyzed step be carried out at the higher temperatures e.g. 50–65 or 78° C., depending on the alcohol and cosolvent. It is not necessary to cool the reaction between the acid-catalyzed and base-catalyzed steps. The reaction may be carried out without substantial agitation of the reaction mixture.

Both catalysts are preferably added to the reaction mixture in the form of a solution, either in the alcohol being used in the reaction or in an alcohol/cosolvent mixture. Heat and stirring may be necessary to dissolve the base catalyst. The alcoholic solution of catalyst is preferably added quickly to the reaction mixture.

As exemplified herein, the base-catalyzed conversion of the triglyceride to the ester is rapid, and a high conversion may be obtained in minutes, depending on the reactants and reaction conditions.

After completion of the reaction, the alcohol e.g. methanol, remaining in the reaction mixture and the cosolvent e.g. tetrahydrofuran (THF) are separated, e.g. by distillation or flashing off. Such distillation or flashing off may be carried out either at atmospheric pressure or at reduced pressure. On removal of the alcohol and cosolvent, a glycerol phase is formed. It has been found that the alcohol and cosolvent may be co-distilled prior to separation of the glycerol layer without any substantial amount of reverse transesterification.

Separation of the glycerol phase may be effected, for instance, under gravity or more preferably by centrifugation.

The remaining layer of the reaction mixture is primarily comprised of fatty acid esters. The fatty acid esters that are obtained typically have boiling points that are substantially higher than those of either the cosolvent or the alcohol.

Hydroxide ion remaining after the reaction may be neutralized by the addition of acid prior to distillation of the cosolvent and excess alcohol.

As exemplified herein, high yields viz. greater than 99%, may be obtained using the process of the present invention. If the product obtained contains trace amounts of residual mono- or di-glycerides, such residual amounts may be removed. One method of removal is use of an adsorbent. Examples of adsorbents include alumina, silica gel and other silicon-based adsorbents e.g. Fluorosil™ adsorbent. In an embodiment of the invention, the product obtained is passed through a column of the adsorbent.

In an industrial process, it is preferred to co-distill the cosolvent and excess alcohol at the end of the reaction, for recycle. The catalyst may then be dissolved in the cosolvent/alcohol solution and added to a reaction vessel containing the source of triglyceride. Additional alcohol and/or cosolvent would be added as required. After the reactants have been mixed in the reaction vessel, stirring may be discontinued.

It is preferred that the purified esters contain no more than 0.25% by weight of total glycerol moieties (including mono- and diglycerides) and no more than 0.03% by weight of free glycerol. Glycerol present in the biofuel can clog injectors of diesel engines. Glycerol is a valuable by-product of the reaction and has many uses such as in resins, pharmaceuticals, soaps, and foods.

The process of the present invention may be operated as a batch process, as a continuous process or as a combination of a batch and continuous process. The latter may be preferred, with the acid catalyzed step being the batch part of the process, as the acid catalyzed step of the process is a slower reaction than the base catalyzed step of the process. It would be preferred to operate the process as a continuous process. The process may be operated over a range of temperatures, as noted above, including ambient temperature and elevated temperatures. At least parts of the process i.e. particularly the base-catalyzed step, could be operated outdoors at ambient temperatures in many parts of the world or at conventional indoor temperature in areas with cooler climates. Operation of the entire process at the temperature preferred for the acid-catalyzed step would increase the rate of reaction.

The process of the present invention gives rapid conversion of fatty acids and fatty acid triglycerides to fatty acid esters, which have a variety of uses. The particularly preferred use is as a biofuel or biodiesel.

The ASTM standard for biodiesel that is currently being evaluated includes a requirement for total glycerol of a maximum of 0.40% by weight. For this calculation, glycerol that is in the form of a mono-(MG), di-(DG) or triglyceride (TG) must be converted to the corresponding amounts of glycerol. The conversion factors vary with the particular moieties of the vegetable oil. For soybean oil, the conversion factors to amount of glycerol are approximately 0.25 for monoglyceride, 0.14 for diglyceride and 0.10 for triglyceride. German biodiesel standard DIN V 51606 imposes an upper limit of 0.23% (wt) of glycerol.

The present invention is illustrated by the following examples:

EXAMPLE I

This example illustrates the conversion of fatty acid triglycerides to the methyl esters, i.e. the base-catalysed step of the process. Transesterification of soybean oil is exemplified, using a 6:1 molar ratio of methanol to oil that is according to the prior art as represented by Canadian Patent Application 2 131 654, and using higher ratios.

The soybean oil was a food-grade product and was obtained as President's Choice™, Sunfresh Ltd., Toronto, Ontario, Canada. Solvents were as follows: methanol (anhydrous, 99+%), tetrahydrofuran (anhydrous, 99+%). methyltertiary butyl ether (anhydrous, 99+%), bis (trimethylsilyl) trifluoroacetamide (BSTFA, 99+%), pyridine (anhydrous 99+%. Analytical grade sodium hydroxide (98%), concentrated hydrochloric acid, and anhydrous sodium sulfate were obtained from BDH Inc. (Toronto, Ontario, Canada).

Gas chromatography (GC) analyses of transesterified methylated products were performed on a Hewlett-Packard (Palo Alto, Calif.) 5880A series gas chromatograph equipped with an on-column injector, a flame-ionization detector (FID) and a BD-1 fused-silica capillary column (2 m×0.25 mm i.d.) coated with 0.25 µm film of 100% polymethyl siloxane.

For transesterification of soybean oil, soybean oil (100 g) and anhydrous THF (45 mL) were placed in a 500-mL flat-bottom flask equipped with a magnetic stirrer and the mixture was stirred. Sodium hydroxide [1.0 g (1.0 wt % with respect to soybean oil)] solution in methanol [28 mL (6:1 methanol-to-oil)] was then added and the stirring was continued for an additional 20 s. Samples of the reaction mixture were taken at 3, 5, 10, 20 30, 60 and 120 minutes and quenched immediately into 125-mL Erlenmeyer flasks containing water (20 mL). The ester remained in the upper organic layer in the reaction mixture, thus allowing titration of the hydroxide ion in the water phase.

Anhydrous sodium sulfate was added to each of the vials to absorb the trace amount of moisture. The samples were then derivatized for GC analyses. The derivatization of the organic material was necessary in order to determine the amount of mono-and diglycerides present in the final product by GC. Mono-and diglycerides are sufficiently volatile for GC analysis: the addition of BSTFA reagent made them more volatile so that they could be detected by the GC.

For derivatization, anhydrous pyridine (0.4 mL) and BSTFA reagent (0.2 mL) were added to each 20-mL vial containing transesterified product (100 mg). The vials were then capped, shaken and placed on a water bath at 65° C. for 20 min. with occasional stirring. After heating, the samples were removed from the water bath, cooled to room temperature and diluted using THF (4.4 mL). The samples were then injected into the gas chromatograph to obtain a profile of the conversion of methyl ester with respect to time.

The change in hydroxide concentration in the one-phase methanolysis reaction was measured directly at room temperature (23° C.). In addition to the above, a number of transesterification reactions were carried out using soybean oil, methanol, and four different concentrations of sodium hydroxide catalyst (1.1, 1.3, 1.4, and 2.0 wt %). All other experimental conditions including the methanol-to-soybean oil molar ratio (6:1) were the same as described above for soybean oil.

Figure 2:
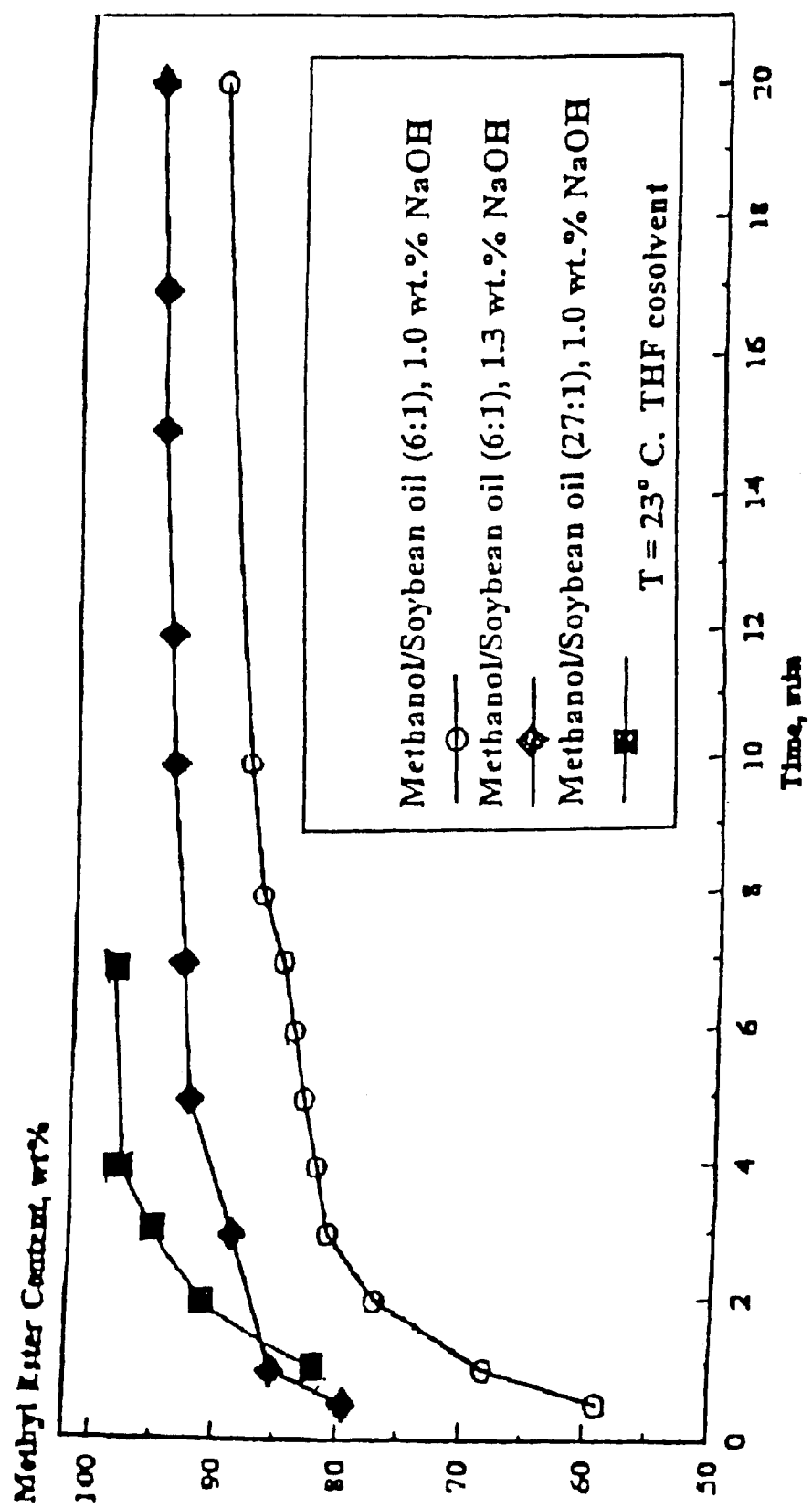
FIG. 2 is a graphical representation of a one-phase methanolysis of soybean and coconut oils, according to the prior art and to the present invention.

The results obtained are shown in FIGS. 1–2. A typical hydroxide depletion curve for the one-phase methanolysis of soybean oil at 23° C. (6:1 methanol/oil molar ratio and 1.0 wt % sodium hydroxide based on the oil) is shown in FIG. 1. Methyl ester production for soybean oil is shown in FIG. 2. Results for soybean oil in which 1.3 wt % sodium hydroxide was used, are also shown in FIG. 2.

Using the above procedures, a comparison of the reaction was made using a methanol/soybean ratio of 8:1 with a ratio of 6:1. It was found that the reaction at a molar ratio of 8:1 provided an ester content after one hour of 97.5 wt %, compared to 93.7 wt % for a 6:1 molar ratio. However, after four hours the ester contents were essentially the same.

To further illustrate the base catalyzed step, a number of experiments were also conducted using higher methanol-to-soybean oil molar ratio (25:1, 27:1, 28:1, 35:1, and 40:1) than the conventional 6:1 ratio illustrated above. 1.0 wt % sodium hydroxide was used as catalyst.

The amount of THF needed to obtain the mixture in a single phase in the different methanol-to-oil molar ratio combinations was determined by a cloud point method. The ratios are shown in Table 1.

TABLE 1

Volumes of Methanol and Tetrahydrofuran (THF) Used for Different Molar Ratios of Methanol to Soybean Oil[1]

| Molar Ratio | Volume of methanol (mL) | Volume of THF (mL) |
|---|---|---|
| 25:1 | 23.3 | 20.0 |
| 27:1 | 25.2 | 22.0 |
| 28:1 | 26.2 | 25.0 |
| 35:1 | 32.8 | 26.0 |
| 40:1 | 37.3 | 28.0 |

[1]Volume of oils is 23 mL in all cases.

The reaction procedure described above was repeated, except for the ratio of methanol to triglyceride and the amount of co-solvent.

The results obtained are shown in Table 2. Table 2 shows the results from transesterification reactions of soybean oil involving higher methanol-to-oil molar ratios than the conventional 6:1 ratio. These results are further illustrated in FIG. 2.

TABLE 2

Composition of Methyl Esters in the Products Obtained from Transesterification Reactions of Soybean Oil with Methanol Using Different Methanol/Oil Molar Ratios and 1.0 wt % NaOH Catalyst

| Time (min.) | Methyl esters (%) at different methanol/oil molar ratios | | | | |
|---|---|---|---|---|---|
| | 25:1 | 27:1 | 28:1 | 35:1 | 40:1 |
| 1 | 83.3 | 82.0 | 80.6 | 73.6 | 63.7 |
| 2 | 89.3 | 90.9 | 89.5 | 88.2 | 79.7 |
| 3 | 90.2 | 95.3 | 95.1 | 91.8 | 86.2 |
| 4 | 91.3 | 98.2 | 97.1 | 95.7 | 95.5 |
| 5 | 94.7 | 98.3 | 98.0 | 96.2 | 95.0 |
| 7 | NA[2] | 99.4 | 99.2 | NA | NA |

[2]NA = Not available

The results of Table 2 show that increasing the methanol to oil ratio into the range of 15:1 to 35:1 and particularly in the range of 25:1 to 30:1 resulted in a substantial increase in the amount of methyl ester. In particular, results at 27:1 and 28:1 showed 99.4 and 99.2% conversion, respectively, in a period of only 7 minutes. This is a higher conversion in substantially shorter reaction times than obtained using the procedures of the prior art as described above.

EXAMPLE II

This example illustrates the process of the present invention on a waste product obtained from a cafeteria. The waste product contained 14% by weight of fatty acids.

In the first step of the process, the cafeteria waste sample (100 g) was mixed with 118.7 mL anhydrous methanol, 80 mL anhydrous tetrahydrofuran (THF), and 2 wt % sulphuric acid (2.0 g) in a 500 mL two-necked round-bottom flask, equipped with a condenser, thermometer, and a calcium chloride guard tube. The mixture was heated at 60° C. for 45 min.

In the second step of the process, a sodium hydroxide solution (2.72 g sodium hydroxide in 6.9 mL anhydrous methanol) was added to the flask and the mixture was allowed to stand at the same temperature for 10 min. The amount of sodium hydroxide was necessary to neutralize the mineral acid and the unreacted fatty acids from the first step, and to catalyse the transesterification reaction.

Solvents were removed in a rotary evaporator using a water bath at 70° C. and reduced pressure. A glycerol layer separated out at the bottom of the flask and the upper layer (methyl esters) were decanted into a 1 L separatory funnel containing 400 mL 1N hydrochloric acid. The mixture was shaken vigorously and allowed to stand for 15 min. The aqueous portion was discarded and the organic layer was washed four times with distilled water (4×250 mL). The aqueous layer was again discarded and the organic layer was dried in a rotary evaporator using a water bath (~100° C.) and reduced pressure.

Purity of the products was verified by gas chromatography after derivatization with BSTFA (bis(trimethylsilyl) trifluoroacetamide) reagent. The product contained 99.24% of the methyl ester, and 0.52% of the monoglyceride. Diglyceride and triglyceride were not detected.

EXAMPLE III

This example illustrates the process of the present invention on a 50:50 (w/w) mixture of soybean oil and palmitic acid.

In the first step of the process, a sample containing soybean oil and palmitic acid (100 g, 50:50 w/w) was mixed with 135 mL anhydrous methanol, 69.5 mL anhydrous tetrahydrofuran (TFH), and 2 wt % sulphuric acid (2.0 g) in a 500 mL two-necked round-bottom flask, equipped with a condenser, thermometer, and a calcium chloride guard tube. The mixture was heated at 60° C. for 45 min.

In the second step of the process, a sodium hydroxide solution (2.74 g sodium hydroxide in 7.0 mL anhydrous methanol) was then added to the flask and the mixture was allowed to stand at the same temperature for 10 min. The amount of sodium hydroxide was necessary to neutralize the mineral acid and any unreacted fatty acids, and to catalyse the transesterification reaction.

Solvents were removed in a rotary evaporator using a water bath at 70° C. and reduced pressure. In this case a glycerol layer was not separated because of the presence of the methyl esters of palmitic acid, which have a m.p. 32–34° C. The whole mixture was melted and transferred into a 1 L separatory funnel containing 400 mL 1 N hydrochloric acid. The mixture was shaken vigorously and allowed to stand for 2 h, for better phase separation. The aqueous portion was discarded and the organic layer was washed four times with hot distilled water (4×250 mL). The aqueous layer was again discarded and the organic layer was dried in a rotary evaporator using a water bath (~100° C.) and reduced pressure.

Purity of the product was verified by gas chromatography after derivatization with BSTFA (bis(trimethylsilyl) trifluoroacetamide) reagent. The product contained 99.62% of methyl ester, and 0.38% of monoglyceride. Diglyceride and triglyceride were not detected.

EXAMPLE IV

This example illustrates the process of the present invention on a 44:56 (w/w) mixture of soybean oil and palmitic acid.

In the first step of the process, a sample containing soybean oil and palmitic acid (100 g, 44:56 w/w) was mixed with 136.4 mL anhydrous methanol, 60 mL anhydrous tetrahydrofuran (THF), and 2 wt % sulphuric acid (2.0 g) in a 500 mL two-necked round-bottom flask, equipped with a condenser, thermometer, and a calcium chloride guard tube. The mixture was heated at 60° C. for 45 min.

In the second step of the process, a calculated amount of sodium hydroxide solution (2.76 g sodium hydroxide in 7.0 mL anhydrous methanol) was added to the flask and the mixture was allowed to stand at the same temperature for 10 min. The amount of sodium hydroxide was necessary to neutralize the mineral acid and any unreacted fatty acids, and to catalyse the transesterification reaction.

Solvents were removed in a rotary evaporator using a water bath at 70° C. and reduced pressure. A glycerol layer was not separated because of the presence of the methyl esters of palmitic acid, which have a m.p. 32–34° C. The whole mixture was melted and transferred into a 1 L separatory funnel containing 400 mL 1 N hydrochloric acid. The mixture was shaken vigorously and allowed to stand for 2 h (for better phase separation). The aqueous portion was discarded and the organic layer was washed four times with hot distilled water (4×250 mL). The aqueous layer was again discarded and the organic layer was dried in a rotary evaporator using a water bath (~100° C.) and reduced pressure.

Purity of the product was verified by gas chromatography after derivatization with BSTFA ((bis(trimethylsilyl) trifluoroacetamide) reagent. The product contained 99.64% of methyl ester and 0.3% of monoglyceride. Diglyceride and triglyceride were not detected.

EXAMPLE V

This example illustrates the process of the present invention with a grease trap waste that contained 97% fatty acids.

In the first step of the process, a treated grease trap waste sample (100 g) which had been phase-separated from water by melting, was mixed with 134.5 mL anhydrous methanol, 40 mL anhydrous tetrahydrofuran (THF) and 2 wt % sulphuric acid (2.0 g) in a 500 mL two-necked round-bottom flask, equipped with a condenser, thermometer, and a calcium chloride guard tube. The mixture was heated at 60° C. for 45 min.

In the second step of the process, a sodium hydroxide solution (2.86 g sodium hydroxide in 7.3 mL anhydrous methanol) was added to the flask and the mixture was allowed to stand at the same temperature for 10 min. The amount of sodium hydroxide was necessary to neutralize the mineral acid and any unreacted fatty acids, and to catalyse the transesterification reaction.

Solvents were removed in a rotary evaporator using a water bath at 70° C. and reduced pressure. A glycerol layer separated at the bottom of the flask and the upper layer (methyl esters) was decanted into a 1 L separatory funnel containing 400 mL 1 N hydrochloric acid. The mixture was shaken vigorously and allowed to stand for 6 h. The aqueous portion was discarded and the organic layer was washed four times with hot distilled water (4×250 mL). The aqueous layer was again discarded and the organic layer was dried in a rotary evaporator using a water bath (~100° C.) and reduced pressure.

Purity of the product was verified by gas chromatography after derivatization with BSTFA ((bis(trimethylsilyl) trifluoroacetamide) reagent. The product contained 99.21% of methyl ester, 0.32% of monoglyceride and 0.47% of diglyceride.

EXAMPLE VI

This example illustrates the process of the present invention with the alcohol being ethanol and the base catalyst being potassium hydroxide.

A sample containing soybean oil and palmitic acid (100 g, 50:50, w/w) was mixed with 176 mL anhydrous ethanol, 17.5 mL anhydrous tetrahydrofuran (THF) and 2 wt % sulphuric acid (2.0 g) in a 500 mL two-necked round-bottom flask, equipped with a condenser, thermometer, and a calcium chloride guard tube. The mixture was heated at 75° C. for 45 min.

A potassium hydroxide solution (4.59 g KOH in 27.5 mL anhydrous ethanol) was then added to the flask and the mixture was allowed to stand at the same temperature for 10 min. The amount of KOH was sufficient to neutralize the mineral acid and unreacted palmitic acid, and to catalyze the transesterification of triglycerides.

Solvents were then removed under reduced pressure in a rotary evaporator, using a water bath at 80° C. The glycerol layer was not separated out because the ethyl ester of palmitic acid has a m.p. of 26–28° C. The whole mixture was melted and transferred into a 1 L separatory funnel containing 400 mL 1N HCl. The mixture was shaken vigorously and allowed to stand for 2 h, for phase separation. The aqueous portion was discarded and the organic layer was washed 4 times with hot distilled water (4×250 mL). The aqueous layer was again discarded and the organic layer was dried in a rotary evaporator using a water bath (~100° C.) and reduced pressure.

Purity of the product was verified by gas chromatography via derivatization with BSTFA (bis(trimethylsilyl) trifluoroacetamide) reagent. The product contained 98.1% of methyl ester, 1.4% of monoglyceride and 0.5% of diglyceride. Triglyceride was not detected.

What is claimed is:

1. A single liquid phase process for the esterification of a mixture of fatty acids and triglycerides, comprising:
   (a) forming a solution of said fatty acids and triglycerides, an alcohol, an acid catalyst and a cosolvent at a temperature that is less than the boiling point of the solution, said alcohol being selected from the group consisting of methanol, ethanol, and mixtures thereof, and the molar ratio of the alcohol to the triglycerides plus one third of the fatty acids being in the range of 15:1 to 35:1, the cosolvent being in an amount to effect formation of a single liquid phase;
   (b) maintaining the solution for a period of time to effect acid-catalyzed esterification of the fatty acids;
   (c) neutralizing the acid catalyst and adding a base catalyst for the transesterification of the triglycerides; and
   (d) after a further period of time, separating esters from said solution.

2. The process of claim 1 in which the solution contains less than 1% by weight of water.

3. The process of claim 2 in which the solution contains less than 0.5% by weight of water.

4. The process of claim 2 in which the alcohol is methanol.

5. The process of claim 2 in which the alcohol is ethanol.

6. The process of claim 2 in which the alcohol is a mixture of ethanol and methanol.

7. The process of claim 2 in which the acid catalyst is anhydrous sulphuric acid.

8. The process of claim 2 in which the base catalyst is selected from sodium hydroxide and potassium hydroxide.

9. The process of claim 7 in which the solution of (a) is neutralized with an alkali metal compound that forms a sulphate.

10. The process of claim 9 in which the alkali metal compound is sodium or potassium carbonate.

11. The process of claim 4 in which the molar ratio of alcohol to fatty acid plus triglyceride is in the range of 20:1 to 30:1.

12. The process of claim 11 in which the molar ratio of alcohol to fatty acid plus triglyceride is in the range of 25:1 to 30:1.

13. The process of claim 11 in which the triglyceride has fatty acid moieties that are $C_{16}$ or higher.

14. The process of claim 11 in which the triglyceride is selected from the group consisting of beef tallow, coconut oil, corn oil, cottonseed oil, lard, olive oil, palm oil, palm kernel oil, peanut oil, soybean oil, linseed oil, tung oil, sunflower oil, safflower oil, canola oil, rapeseed oil, sesame oil, babassu oil, perilla oil, oiticica oil, fish oils, menhaden oil, castor oil, Chinese tallow tree oil, Physic nut oil, Cuphea seed oil, microalgal oils, bacterial oils and fungal oils.

15. The process of claim 11 in which the cosolvent is a cyclic ether.

16. The process of claim 11 in which the cosolvent is selected from the group consisting of tetrahydrofuran, 1,4-dioxane, diethyl ether, methyltertiarybutylether and diisopropyl ether.

17. The process of claim 11 in which the temperature is in the range of from 15° C. to 65° C.

18. The process of claim 11 in which the temperature is at least 50° C.

19. The process of claim 11 in which the temperature is at least 60° C.

20. The process of claim 11 in which ester is recovered in a yield of at least 99%.

21. The process of claim 1 in the form of a continuous process.

22. A biofuel comprising an ester with a glycerol content of less than 0.40% by weight, said ester having been obtained by a process of claim 1.

23. The biofuel of claim 22 in which the glycerol content is less than 0.23% by weight.

* * * * *

UNITED STATES PATENT AND TRADEMARK OFFICE
CERTIFICATE OF CORRECTION

| | |
|---|---|
| PATENT NO. | : 6,642,399 B2 |
| APPLICATION NO. | : 10/199359 |
| DATED | : November 4, 2003 |
| INVENTOR(S) | : David Gavin Brooke Boocock |

It is certified that error appears in the above-identified patent and that said Letters Patent is hereby corrected as shown below:

<u>Title Page</u>
    [73] Assignee, insert --Biox Corporation (CA)--.

<u>Column 6</u>
    Line 62 "99+%." should read --99+%.)--.

<u>Column 10</u>
    Line 20 "((bis" should read --(bis--.
    Line 57 "((bis" should read --(bis--.

Signed and Sealed this

Seventeenth Day of July, 2007

JON W. DUDAS
*Director of the United States Patent and Trademark Office*